United States Patent [19]
Las Navas Garcia

[11] Patent Number: 5,355,721
[45] Date of Patent: Oct. 18, 1994

[54] METHOD AND APPARATUS FOR MEASURING DEPTH AND HARDNESS

[76] Inventor: Jose M. Las Navas Garcia, Parque Infantas 150, 28210 Valdemorillo, Madrid, Spain

[21] Appl. No.: 129,682

[22] Filed: Sep. 30, 1993

[30] Foreign Application Priority Data

Dec. 18, 1992 [EP] European Pat. Off. ......... 92500167.9
Mar. 1, 1993 [EP] European Pat. Off. ......... 93500025.7

[51] Int. Cl.$^5$ .............................................. G01N 3/48
[52] U.S. Cl. ........................................................ 73/82
[58] Field of Search ...................................... 73/81–83

[56] References Cited

U.S. PATENT DOCUMENTS

| | | | |
|---|---|---|---|
| 3,365,937 | 1/1968 | Miserocchi | 73/81 |
| 3,406,566 | 10/1968 | Livingston et al. | 73/81 |
| 3,877,298 | 4/1975 | Narang | 73/81 |
| 4,611,487 | 9/1986 | Krenn et al. | 73/81 |

FOREIGN PATENT DOCUMENTS 8800691  1/1988  World Int. Prop. O. ............. 73/82

Primary Examiner—Robert Raevis
Attorney, Agent, or Firm—Steven H. Bazerman

[57] ABSTRACT

A method and apparatus of measuring the hardness or various other characteristics of a sample surface, comprises a load cell carrying a penetrator and connected to a computer for reading signals from the load cell. The sample is advantageously mounted on the vertically moveable table of a microscope. The table can be moved by a stepper motor also connected to the computer for raising the sample into contact with the penetrator until a preselected force is reached. The force is sufficient to indent the sample surface with the penetrator. Optical or other mechanisms can then be used to measure the indentation. One other mechanism which can be used to measure the indentation is a second load cell carrying a tube which also contacts the sample surface and produces a second signal. Signals from the two load cells can be processed to measure a difference between the signals which provides a measurement of the indentation produced by the penetrator.

11 Claims, 4 Drawing Sheets

METHOD AND APPARATUS FOR MEASURING DEPTH AND HARDNESS

FIELD AND BACKGROUND OF THE INVENTION

The present invention relates, in general, to a method and apparatus for measuring depth of penetration and hardness into and of a material to be tested. In particular, the method and apparatus of the invention utilizes responds to a signal from a load cell that indicates a force applied to a tool for making an indentation on a sample of the material. The signal discontinues the force when a set point has been reached and depth of penetration, and/or hardness is measured either optically or by using a second load cell in an inventive arrangement.

Present systems used to measure the hardness or micro-hardness of, particularly, metallic samples are known as the Brinell, Vickers or Rockwell systems. Each of these requires that a known weight be placed on top of a ball or diamond penetrator which contacts the surface of a sample, to create an indentation in the sample. The weight and penetrator are then removed and the sample transferred to optical computation apparatus to calculate the hardness of the sample from an optical determination of the size of the indentation made in the sample by the weight and penetrator.

SUMMARY OF THE INVENTION

It is an object of the present invention to avoid weight-operated indentation devices and, preferably, to automate or semi-automate the hardness-measuring technique. One embodiment of the invention also avoids optical computation used by the prior art to calculate hardness.

To these and other ends, the invention provides a method in which a penetrator is mounted on a load cell apparatus. A sample surface is brought in contact with the penetrator. The load cell produces a signal proportional to an increasing force being applied between the penetrator and a sample surface. When the signal indicates that a predetermined force has been reached between the penetrator and the sample, the force is discontinued in response to the signal. An alternative embodiment produces a signal from the load cell only when the force reaches the predetermined value. An indentation produced in the sample by the penetrator and force, is then optically measured in a known manner, according to one embodiment of the invention.

According to another embodiment of the invention, two load cells are needed. A penetrator is mounted to one of the load cells. A sample surface is brought in contact with the penetrator. The load cell produces a signal proportional to increasing force between the penetrator and the sample. When the signal indicates that a predetermined force is being applied between the penetrator and sample, the force is discontinue in response to the signal. Simultaneously, the other load cell which carries a ring that is in non-penetrating contact with the sample surface, is producing a second signal that is proportional to the increasing force between the ring and the sample. If neither load cell was carrying a penetrator, the two signals would be equal to each other and independent of displacement of the sample up or down. With a penetrator tool mounted to one of the load cells, as the sample is moved upwardly the tool penetrates the sample surface and a difference in the signals from the two cells is proportional to the depth of penetration created by the tool. The depth thus being measured, allows for a calculation of the hardness of the material without the need for optical measurements.

Accordingly, a further object of the present invention is to provide a method and apparatus for measuring the depth of penetration and/or hardness of a sample material, which apparatus is simple in design, rugged in construction and economical to manufacture.

An important distinction of the invention over the prior art is that force is being applied to the penetrator through a precise load cell rather than by a weight.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which multiple embodiments of the invention are illustrated.

BRIEF DESCRIPTION OF THE DRAWINGS

Preferred embodiments that illustrate, but do not limit the invention, will now be described with reference to the drawings wherein.

DESCRIPTION OF THE PREFERRED EMBODIMENTS

Figure 2:
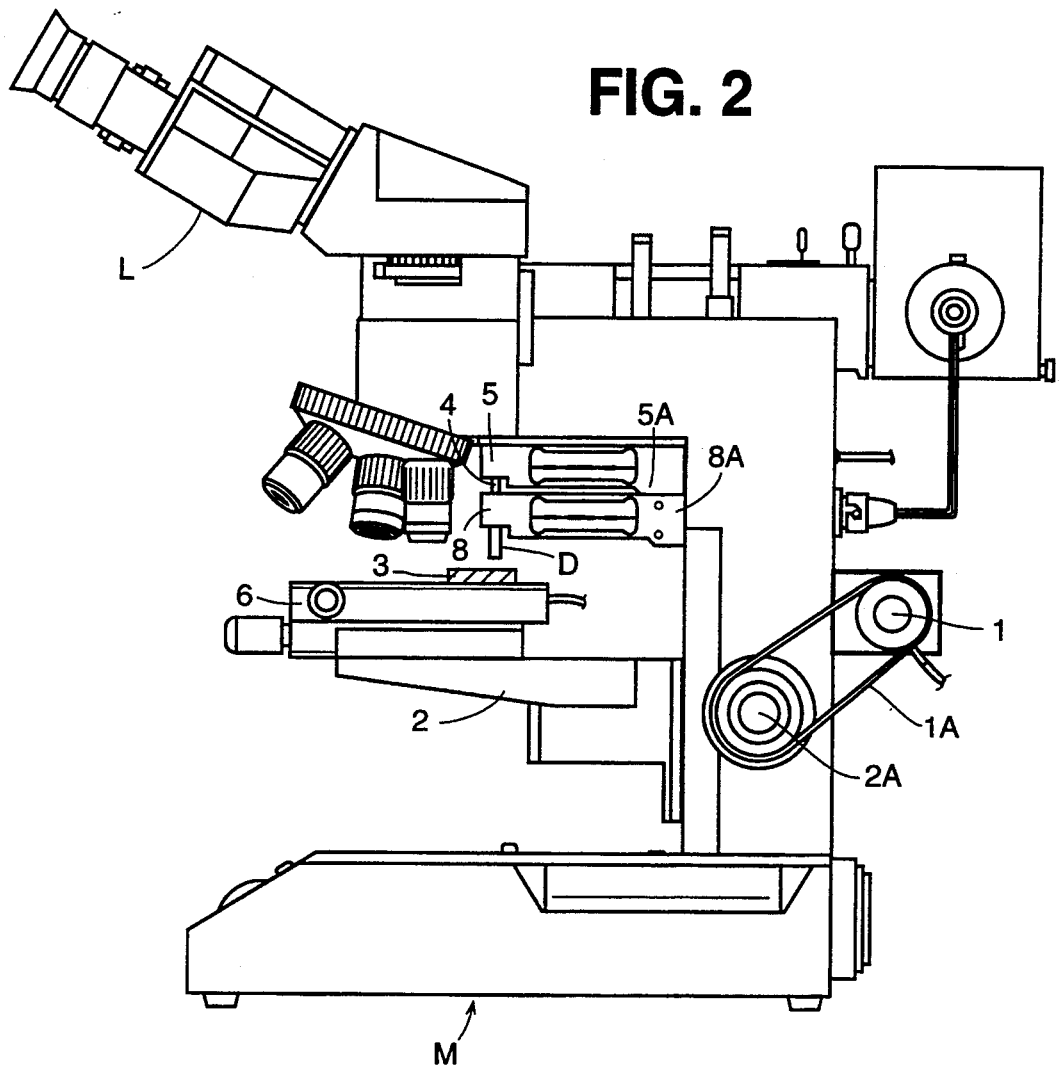
FIG. 2 is a side-elevational view of the apparatus used for applying forces to the surface of a sample whose hardness is to be tested, including in part, a commercially available microscope with movable stage.

FIG. 2 shows a microscope at M. The microscope is preferably a model Examet microscope manufactured by Union Optical Co., Ltd., of Tokyo, Japan, with a reflected light, head. However, any suitable microscope may be used.

The microscope has a knob 2A, and by rotating of the knob, a microscope table 2 is moved along the optical path of the microscope, i.e. vertically as shown in FIG. 2.

A stepper motor 1 is mounted on one side of the microscope together with a belt 1A engaged between the stepper motor and the knob 2A. Rotation of the stepper motor rotates the knob via the belt to move the microscope table 2, as described above. As an example, the stepper motor may be a Phytron model ZSS motor. The arrangement of the belt 1A between the stepper motor and the knob is well understood and no further descriptions is provided here.

The surface of the microscope table 2 in the optical path of the microscope, i.e., the upper side of the table in FIG. 2, has a motorized, movable stage 6. The motorized stage 6 moves a sample 3 of material to be tested, from one indentation position to the next, according to a computer program and for a position aligned with a penetrator 4, to a position in the optical path for optical observation of the indentation(s). For example, the stage 6 can be the one manufactured by Markhauser, as its Model MT mot. 50×50.

The penetrator 4 is mounted on a load cell 5. The penetrator 4 may be diamond shaped according to the Vickers and Knopp systems or rod-shaped according to the Brinell and Rockwell systems. For example, such penetrators are manufactured by Albert Ernehm.

The load cell 5 produces an analog signal proportional to force applied to the penetrator in the direction of movement of the microscope table 2, i.e. vertically in FIG. 2. For example, the load cells manufactured by Huntleigh, Model 505H are suitable.

Figure 3:
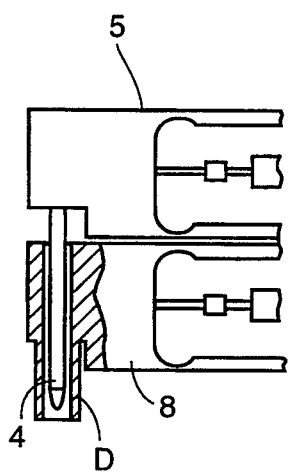
FIG. 3 is an enlarged detail of the load cells used in the embodiment of FIG. 2.

Referring to FIGS. 2 and 3, a second load cell 8 produces an analog signal proportional to force applied to a tube D in the direction of movement of the microscope table 2, i.e., vertically in FIG. 2. This load cell may also be one manufactured by Huntleigh (Model 505H). Tube or ring D engages a large surface of sample 3 and does not, penetrate the sample. Tube D is a surface contactor for contacting the sample surface.

The microscope M has a lens and light arrangement L by which the sample surface may be observed.

Figure 1:
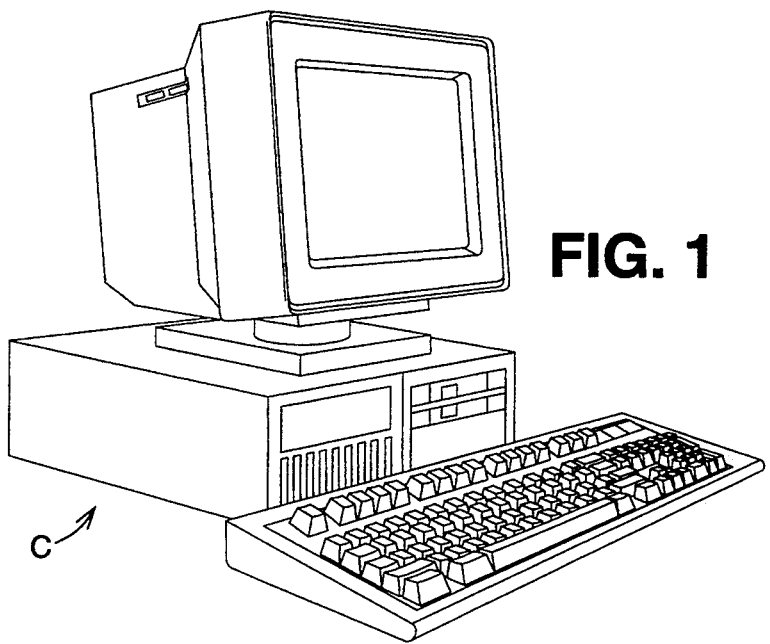
FIG. 1 is a representation of a personal computer or PC which can be used as part of the apparatus for practicing the present invention.
Figure 6:
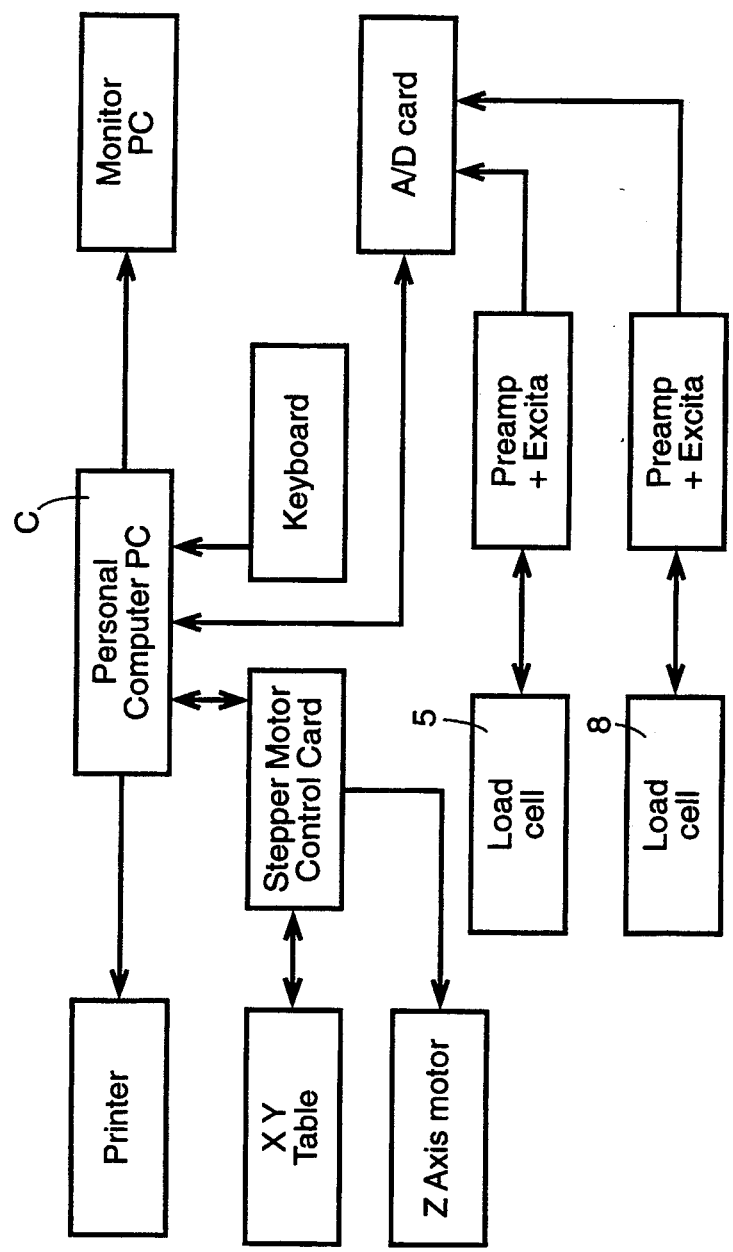
FIG. 6 is a block diagram illustrating the method and apparatus of the present invention embodied in FIG. 2.

The stepper motor 1, motorized stage 6, load cell 5, and load cell 8, are all connected by respective cables to a personal computer C as illustrated in FIGS. 1 and 6, such as the IBM 386 shown in FIG. 1.

In operation, the sample 3 is placed on the motorized stage 6 and the motorized stage 6 is positioned, if necessary, by control from the personal computer, for the sample 3 to be under the penetrator 4 and tube D before the microscope table 2 is moved upwardly. The computer C then operates the stepper motor 1 to move the table 2 upwardly. The upward movement of the microscope table 2 then causes the sample 3 to contact the tube D, The force of contact between the sample and the tube D continues to increase as the stepper motor continues to operate. At the precise moment when the sample 3 is in contact with the penetrator 4, the readings from both cells are recorded by computer C.

The corresponding analog signal from load cell 5 to the computer continues to increase with the increasing force until the signal reaches a value which is preset in the computer to correspond to a predetermined desired force. Data for calibrating the signal from the load cells to the particular force between the sample and the penetrator and tube is supplied by the manufacturer of the load cells. In addition, force to signal calibration techniques are well known to those skilled in the art to require further description. The analog signal from the load cell 5 can be converted by standard methods into a digital signal for use by the computer in its calculations.

When the signal from load cell 5 reaches the predetermined value, the computer is programmed to stop the stepper motor. The program of the personal computer further reverses the stepper motor to lower the microscope table at least sufficiently to avoid further contact between the sample 3 and the penetrator 4 and tube D. The program in the personal computer then causes the motorized table to move the sample to the next indentation site, or to the optical path for visual observation.

The program in the personal computer takes the readings of both load cells 5 and 8 when the load cell 5 with the penetrator 4 reached the predetermined value set in the computer. A routine of the program of the personal computer calculates the hardness of the material of the sample from the initial readings of both load cells and the later readings of both load cells when the predetermined value was reached. The difference in values is proportional to the depth created by the penetrator in the sample surface. The exact relationship depends on the configuration of the penetrator.

Both load cells 5 and 8, have base portions 5A and 8A respectively, which are fixed to the microscope M, and operating ends which are free to move vertically where sending a signal to computer C, which is proportional to the force being exerted against the load cell. In this way, the pressure being exerted on the surface of sample 3, whether it is by the penetrator 4, or the nonpenetrating ring D, can be measured precisely. As noted above, if both load cells 5 and 8 were carrying a single ring D, the signal from the two load cells would be exactly the same. Because one of the load cells 5 is actually connected to the penetrator 4, the signals are different and this difference is a measurement of the amount of penetration of penetrator 4 into the surface of sample 3.

The exact relationship between the readings from the load cells and the depth of penetration can be ascertained empirically. The load cells of the present invention are linear devices. If you read one volt for a load of 1,000 grams, you would get 2 volts from a load of 2,000 grams. They are also mechanically linear. If on a particular load cell, 1,000 grams would result in a 1 mm deflection, then a load of 2,000 grams would result in a 2 mm deflection. In the present example of the device, the load cells have a 0.5 mm deflection at 2,000 grams. Thus, if we measured a signal at 1 gram and later took a reading at 2,000 grams, imposed by a stepper motor, we can divide the number of steps by 2,000 and know the number of steps per gram for the machine.

To know the indentation per gram of force, we can us a laser measuring device to measure the deflection when the load reaches 1 gram and another when the load cell reaches 2,001 grams. The difference of the two distances, divided by 2,000, is the distance per gram. Accordingly, if we know the number of steps per gram and the distance per gram, we could also know the distance per step. By concentrically mounting the diamond-shaped support of penetrator 4, inside tube D, approximately the same surface area of sample 3 is being touched to avoid errors due to inconsistencies across the surface as the penetrator 4 moves into the sample, the load cells are studied at different lengths and a signal showing the difference in voltage between the two load cells and thus be representative of the depth of penetration. When used with a stylus instead of a diamond and pressing table under smaller loads, the present invention can also be used for measuring flatness, roundness, roughness or layer thickness of the sample 3

Thus, the depth measurement can be taken by simply subtracting the amplitudes of the signals of load cells 5 and 8. Hardness can be calculated as a known function of depth of penetration (as measured above) and load applied (which is the load measured by load cell 5). For example, if a calculation of hardness was desired using the Vickers system, it would be noted that Vickers diamonds have 136° angle between faces. Applying basic trigonometry, the relationship between the diagonals and depth is 7, i.e., the depth is seven times smaller than the length of one diagonal. Normal calculations of hardness with the Vickers system is:

$$\text{Hardness} = \frac{\text{Load} \times 1854}{D1 \times D2}$$

Where:
D1 and D2 are diagonals of indentation.
d: is indentation depth.

$$H = \frac{\text{Load} \times 1865}{D1 \times D2} = \frac{\text{Load} \times 1865}{(7 \times d) \times (7 \times d)} = \frac{\text{Load} \times 37.83}{d^2}$$

FIG. 6 shows the functional and hardware aspects of the invention connected to achieve the method of the invention.

It is noted that in all of the figures, the same reference numerals are utilized to designate the same or functionally similar parts.

Figure 4:
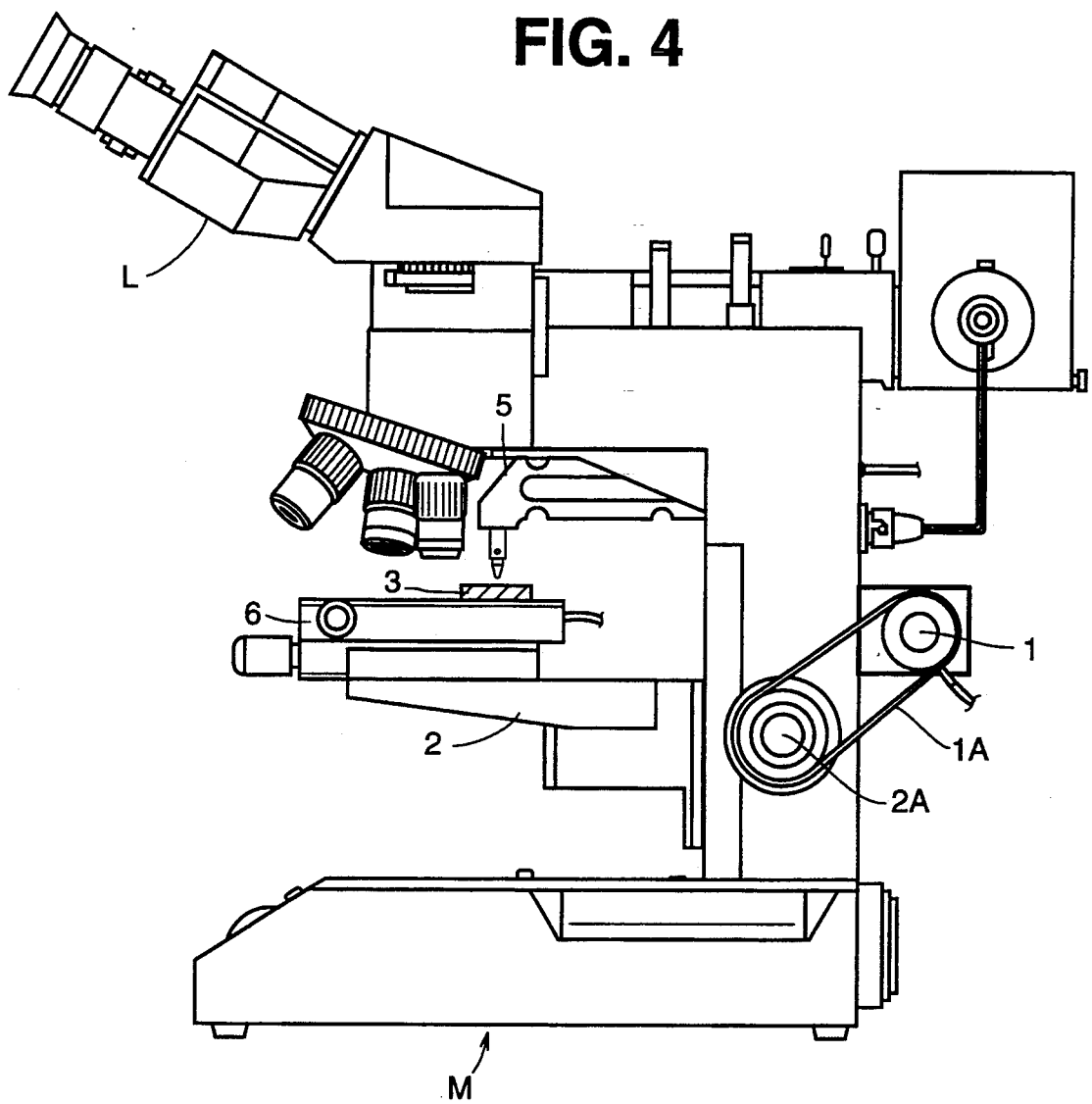
FIG. 4 is a view similar to FIG. 2 of a second embodiment of the present invention.

FIG. 4 also illustrate microscope M set up to practice another embodiment of the invention.

The microscope has a knob 2A. By rotation of the knob, microscope table 2 is moved along the optical path of the microscope, i.e. vertically as shown in FIG. 4 as in the embodiment of FIG. 2.

Figure 5:
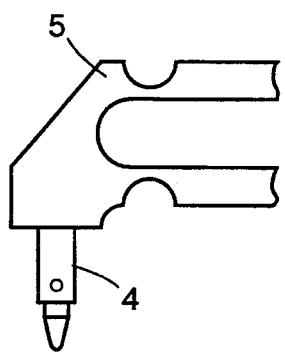
FIG. 5 is an enlarged detail of the load cells used in the apparatus of FIG. 4.

As before, the load cell 5 (FIG. 5) is connected to the computer C and produces an analog signal that is proportional to force applied to the penetrator in the direction of movement of the microscope table 2, i.e. vertically.

The microscope has a lens and light arrangement L by which the optical path of the microscope may be observed. The microscope also has a video camera 7 that also observes the optical path of the microscope. The video camera can be of the type manufactured by Hitachi.

The stepper model 1, motorized stage 6, load cell 5 and video camera 7 are all connected by respective cables to personal computer C.

Figure 7:
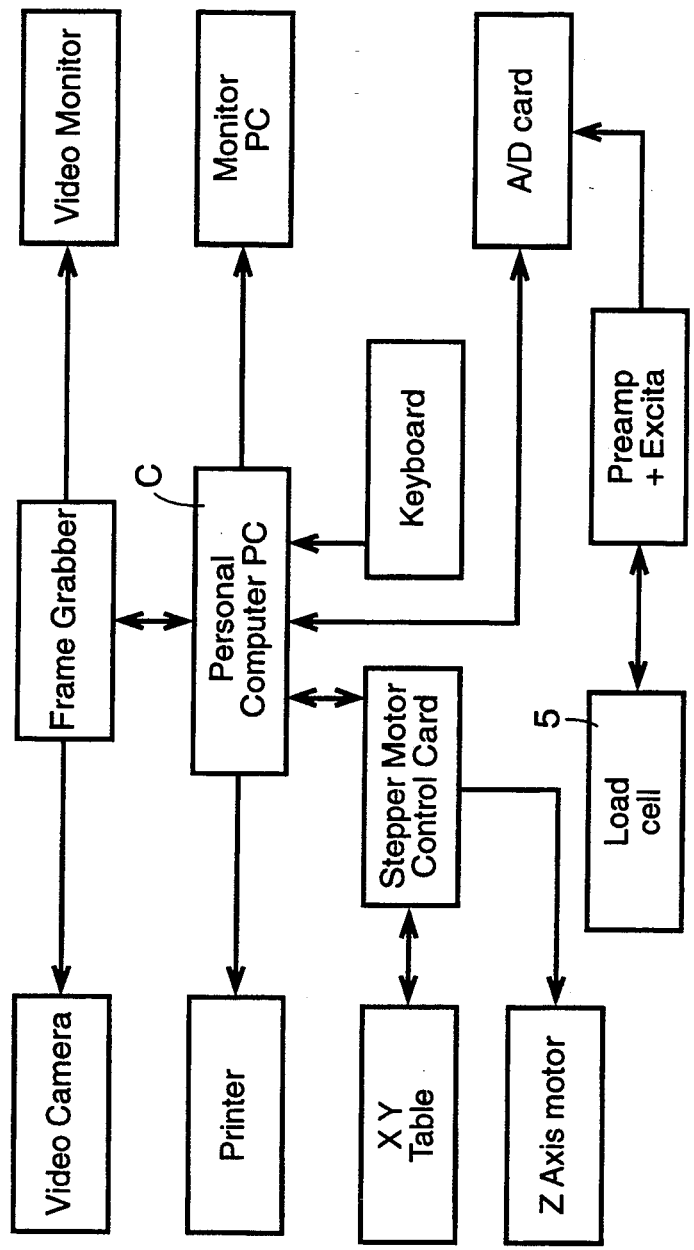
FIG. 7 is a block diagram illustrating the method and apparatus of the invention shown in FIG. 4.

Referring to FIGS. 4 and 7, in operation of the apparatus according to the method, the sample 3 is placed on the motorized stage 6 and the motorized stage 6 positioned, if necessary, by control from the personal computer for the sample 3 to contact the penetrator 4 when the microscope table 2 is moved upwardly. The computer then operates the stepper motor to move the table upwardly.

The upward movement of the microscope table 2 then causes the sample 3 to contact the penetrator 4. The force of the contact between the sample aid the penetrator continues to increase as the stepper motor continues to operate. The corresponding analog signal from the load cell to the computer continues to increase with the increasing force until the signal reaches a value preset in the computer to correspond to a predetermined force. Data calibrating the signal from the load cell to the particular force between the sample and, the penetrator is supplied by the manufacturer of the load cell, but force to signal calibration techniques are well known to those skilled in the art.

When the signal from the load cell reaches the predetermined value set in the computer, the computer is programmed to stop the stepper motor. The program of the personal computer further reverses the stepper motor to lower the microscope table at least sufficiently to avoid further contact between the sample 3 and the penetrator 4. The program for the personal computer then causes the motorized stage 6 to move the sample into the optical path of the microscope. The sample may then be observed through the lens L.

The program for the personal computer also causes the video camera 7 to observe the sample. The program causes the motorized table to move the sample until the video camera observes a field that includes the indentation made in the sample. A field grabber routine allows the computer to obtain information as to the width of penetration from the video image of the indentation. The field grabber program uses standard image analysis and measuring techniques to supply a digital signal corresponding to the width of the penetration. As noted previously, due to the fixed angle of the penetrator 4, this corresponds to the depth of penetration. The personal computer analyzes the resulting digital information as to depth to calculate the hardness of the material of the sample.

While specific embodiments of the invention have been shown and described in detail to illustrate the application of the principles of the invention, it will be understood that the invention may be embodied otherwise without departing from such principles.

What is claimed is:

1. A method of measuring a characteristic at the surface of a sample, comprising:
   placing the sample onto a stage of a microscope which stage is movable in at least one horizontal direction;
   positioning the stage on a vertically movable table;
   moving a sample surface into engagement with a sample surface penetrator by vertically moving the table;
   moving the sample surface with respect to the penetrator by further vertically moving said table;
   measuring the pressure on the penetrator by a load cell;
   stopping vertical movement of the table when a preselected force is reached between the penetrator and the sample surface as measured by the load cell, the preselected force being sufficiently high so that the penetrator produces an indentation in the sample surface;
   removing the sample surface from contact with the penetrator by vertically moving the table; and
   measuring the indentation in the sample surface as a measurement of the characteristic by moving the stage of the microscope in a horizontal direction until the indentation in the sample surface is in alignment with the optical path of the microscope and using the microscope to measure the indentation.

2. A method according to claim 1, wherein the surface characteristic comprises the hardness of the sample surface.

3. A method of measuring a characteristic at the surface of a sample, comprising:
   moving a sample surface into engagement with the sample surface penetrator which is connected to a load cell, the load cell generating signals proportional to a force being exerted on the load cell by the penetrator;
   moving the sample surface with respect to the penetrator until a preselected force is reached between the penetrator as measured by the load cell, and the sample surface, the preselected force being sufficiently high so that the penetrator produces an indentation in the sample surface; and measuring the indentation in the sample surface as a measurement of the characteristic by providing a surface contactor adjacent the penetrator, the surface contactor being connected to a further load cell, moving the sample so that it is in contact with both the penetrator and the surface contactor, and measuring the indentation as a function of a difference between signals from the first mentioned and further load cells.

4. A method according to claim 3, wherein the surface contactor comprises a tube concentrically mounted around the penetrator for contacting the sample surface.

5. A method according to claim 4, including moving the sample surface so that it first comes into contact with the tube and thereafter comes in contact with the penetrator.

6. An apparatus for measuring the surface characteristic of a sample comprising:
 a penetrator adapted for engaging and penetrating a sample surface;
 a load cell connected to said penetrator:
 a movable table means for carrying a sample with a sample surface facing the penetrator;
 first drive means operatively connected to move the table means with respect to the penetrator;
 a movable stage, for positioning the specimen to be tested, mounted on said table means
 a second drive means operatively connected to said table means for positioning said stage; and
 signal processing means connected to and controlling the first and second drive means to cause the table means to move the sample into contact with the penetrator to stop said movement when a preselected force sufficient to cause the penetrator to make an indentation in the sample surface has been reached; to remove the surface of the sample from the perpetrator and to move said stage so that the sample will be positioned to allow the resulting indentation to be optically measured.

7. An apparatus according to claim 6, wherein the table means moves vertically to position the sample against the penetrator, apply pressure to the sample and remove the sample from contact with the penetrator and the stage moves horizontally to position the sample for measurement.

8. An apparatus for measuring the surface characteristic of a sample comprising:
 a load cell;
 a penetrator connected to the load cell and adapted for engaging and penetrating a sample surface;
 table means for carrying a sample with a sample surface facing the penetrator;
 drive means operatively connected to move the table means with respect to the penetrator for engaging the penetrator with the sample surface;
 signal processing means connected to the drive means for moving the table means with respect to the penetrator until a preselected force sufficient to cause the penetrator to make an indentation in the sample surface, has been reached;
 a second load cell,
 a surface contactor connected to the second load cell and positioned adjacent the penetrator for engagement of the sample surface by both the penetrator and the contactor when the table means is moved with respect to the penetrator,
 the signal processing means including means for taking a difference between a signal of the first mentioned and the second load cells as a measurement of the indentation.

9. An apparatus according to claim 8, including a microscope having a support to which the first mentioned and the second load cells are connected, the table means comprising a microscope table mounted for vertical movement to the microscope support, the drive means comprises a motor engaged to the microscope table for moving the microscope table.

10. An apparatus according to claim 9, wherein the penetrator is rod-shaped and the surface contactor is tube-shaped and concentrically mounted around the penetrator.

11. An apparatus according to claim 9, wherein the penetrator is diamond-shaped and the surface contactor is tube-shaped and concentrically mounted around the penetrator.

* * * * *